(12) United States Patent
Weiss et al.

(10) Patent No.: US 6,495,064 B2
(45) Date of Patent: Dec. 17, 2002

(54) ETHYLLITHIUM IN DIBUTYL ETHER

(75) Inventors: Wilfried Weiss, Oberursel (DE); Rainer Aul, Rodgau (DE); Ute Emmel, Frankfurt am Main (DE); Peter Rittmeyer, Sulzbach/Taunus (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 09/862,988

(22) Filed: May 22, 2001

(65) Prior Publication Data

US 2002/0029830 A1 Mar. 14, 2002

(30) Foreign Application Priority Data

Jun. 28, 2000 (DE) .......................... 100 30 535

(51) Int. Cl.[7] .............................. C09K 3/00; C07F 1/02
(52) U.S. Cl. ......................... 252/182.14; 252/182.12; 252/182.29; 252/364; 260/665 R
(58) Field of Search ...................... 252/182.12, 182.29, 252/364, 1, 182.14; 260/665 G, 665 R

(56) References Cited

U.S. PATENT DOCUMENTS

| | | | | |
|---|---|---|---|---|
| 3,772,169 A | * | 11/1973 | Small et al. | |
| 4,588,782 A | * | 5/1986 | Ono et al. | ................... 525/245 |
| 5,149,889 A | * | 9/1992 | Deberitz et al. | ............. 568/878 |
| 5,340,507 A | * | 8/1994 | Morrison et al. | ....... 260/665 R |
| 5,523,447 A | * | 6/1996 | Kamienski et al. | ......... 556/466 |

* cited by examiner

Primary Examiner—Joseph D. Anthony
(74) Attorney, Agent, or Firm—Fulbright & Jaworski L.L.P.

(57) ABSTRACT

This patent describes a solution of ethyllithium in dibutyl ether, a non-pyrophoric solution of ethyllithium in dibutyl ether in a concentration of 7 to 8%, a non-pyrophoric solution of ethyllithium in dibutyl ether and in a hydrocarbon in a concentration of 2 to 8%, process for preparing the solutions and the use of the solutions.

13 Claims, No Drawings

ETHYLLITHIUM IN DIBUTYL ETHER

BACKGROUND AND SUMMARY OF THE INVENTION

This invention relates to a solution of ethyllithium in dibutyl ether.

Ethyllithium (EtLi) is one of the alkyl lithiums. These are used as starters in anionic polymerisation and in preparative organic synthesis. There they are employed as alkylating agents or, because of their strongly basic character, are used for producing carbanions, which can be reacted with a multitude of electrophilic reagents. (Houben-Weyl, Methoden der Organischen Chemie, Thieme Verlag, Volume XIII/1, 1970; Wakefield, B. J., The Chemistry of Organolithium Compounds, Pergamon Press, London, 1974; Organolithium Methods, Academic Press, London, 1988; Brandsma, L., Preparative Polar Organometallic Chemistry, Vol. 1, 1987, and Vol. 2, 1990, Springer Verlag; M. Schlosser et al., Organometallics in Synthesis, 1994, John Wiley & Sons, Sussex).

The preparation of alkyl lithiums according to the equation

2 Li+R—Hal→R—Li+Li—Hal goes back to K. Ziegler (K. Ziegler, H. Colonius, Liebigs Ann. Chem. 476, 135, 1930). The synthesis can be carried out both in hydrocarbons (Gilman, H. et al., JACS, 63, 2479, 1941) and in ethers (Gilman H., JACS, 71, 1499, 1949).

The use of ethers as solvents is extremely limited here because, with the exception of the case of methyllithium in diethyl ether, the alkyl lithium attacks the ether, with the resulting decomposition of the alkyl lithium and cleavage of the ether. (A. Maercker, Ang. Chem. 99, 1002, 1987). For ethyllithium in diethyl ether, the half life period was found to be 54 hours at 25° C. and 17 hours at 35° C. (T. L. Brown et al., JACS, 88, 2174, 1966). In the case of ethyllithium in tetrahydrofuran (THF), the decomposition of THF by ethyllithium with the formation of ethene and Li ethenolate already takes place at −20° C. (A. Rembaum et al., J. Polym. Sci. 56, p. 17, 1962).

Ethereal solutions of ethyllithium are produced in situ as required. A commercial preparation and provision of these solutions has not hitherto been possible.

The possibility of using hydrocarbons as solvents for ethyllithium has hitherto been extremely limited, because the solubility of ethyllithium is very low owing to the small alkyl group (solubility in hexane: 2%, in toluene: 4%, in benzene: 5%) and such dilute solutions are uneconomic. Furthermore, a solution of ethyllithium in toluene has the disadvantage that toluene is metalated by ethyllithium. Benzene is hardly suitable as a solvent because of its carcinogenic properties.

Attempts have been made to bring EtLi into solution by complexing with other Li-alkyls, with the aim of producing more highly concentrated ethyllithium solutions (Weiner, West, JACS, 85, 4856, 1963). A disadvantage of such solutions is the presence of other alkyl groups, which make these solutions unsuitable for the introduction of the ethyl group. There have also been attempts to complex EtLi with Li ethoxide and thus to stabilise it (Brown, T. L., JACS, 88, 2174, 1966). Here the altered reactivity of the EtLi is a disadvantage.

The object of the present invention is to eliminate the disadvantages of prior art and, in particular, to provide a relatively stable solution of ethyllithium, without other alkyl groups, having an EtLi concentration of up to 15% (% data, unless indicated otherwise, are wt. %). A further object is to provide a process for preparing such an EtLi solution.

This object is achieved by an EtLi solution in dibutyl ether and by a process for preparing such a solution, in which process lithium in dibutyl ether is reacted with ethyl chloride to form ethyllithium.

DETAILED DESCRIPTION

Surprisingly, it has been found that the EtLi solution according to the invention is relatively stable (see Table 1).

TABLE 1

Decomposition rates of EtLi solution in dibutyl ether and, for comparison, those of EtLi solution in diethyl ether, at various temperatures. (The active base was determined by Gilman's method of double titration (H. Gilman, A.H. Haubein, JACS, 66, 1515, 1944).)

| | Decomposition in mol.% per day | |
|---|---|---|
| Temperature (° C.) | EtLi in dibutyl ether | EtLi in diethyl ether |
| 0 | 0.08 | |
| 20 | 0.21 | |
| 25 | | 30 |
| 35 | | 98 |
| 40 | 2.98 | |
| 50 | 21.5 | |
| 60 | 31 | |
| 70 | 86 | |

For the loss of active base, a first-order reaction is assumed; for this k=[end concentration$_{(active\ base)}$/initial concentration$_{(active\ base)}$]×100/storage time, in days.

The solution of ethyllithium in dibutyl ether is prepared by Ziegler's method. Here the lithium, for example, in the form of a dispersion in dibutyl ether, is placed in a vessel and reacted by introducing gaseous ethyl chloride. In the case of an approximately 90% conversion, a solution having a content of up to 12% ethyllithium is obtained after filtration. The prepared solution having a maximum content of 12% ethyllithium can be concentrated to 15% by evaporation to small volume under vacuum at room temperature.

Owing to the pyrophoric behaviour of these highly concentrated solutions, it is advisable to adjust commercial solutions to an ethyllithium content of 7 to 8%. This can be effected by directly synthesising a 7 to 8% solution or by diluting a more highly concentrated solution to 7 to 8%. The diluents used can be dibutyl ether, or hydrocarbons (cyclic or acyclic) having 5 to 12 C atoms or aromatic hydrocarbons having 6 to 12 C atoms. These solutions are then no longer pyrophoric. Solutions of ethyllithium in dibutyl ether and in one or more hydrocarbons contain preferably 5 to 8% ethyllithium.

Lithium is used preferably as granules (for example, having a particle size of up to 3 mm) and particularly preferably in pulverous form (particle size 10 to 500 μm, preferably 10 to 200 μm), with an excess of lithium generally being used. A stoichiometric quantity of 2 mol Li and in addition an excess of 0.02 to 0.5 mol, preferably 0.02 to 0.3 mol, lithium is used per mol ethyl chloride.

The initial concentration is preferably so chosen that the product concentration in the final solution is approximately 8%. As the reaction of lithium with ethyl chloride is exothermic, the reactants are preferably cooled during the conversion in order to trap the heat of reaction and to avoid secondary reactions and decomposition of the product. The maximum reaction temperature is 40° C. A reaction temperature of −10° C. to +10° C. is preferred. The feed rate is so chosen that the heat of reaction is trapped efficiently and excess ethyl chloride does not escape from the reaction mixture. An excessively rapid metering of the ethyl chloride should be avoided, owing to its solubility in dibutyl ether and a possible Wurtz reaction. The lithium chloride formed during the reaction is filtered off at the end of the reaction; the filtered solution is the final product solution or may, as required, be diluted to the desired concentration using dibutyl ether or a hydrocarbon.

The preferred storage temperature of the solution is −20° C. to +5° C.; a storage temperature of 0° C. is particularly preferred.

The subject matter of the invention is explained in more detail below by means of the following Examples.

DETAILED DESCRIPTION OF PREFERRED EMBODIMENT

EXAMPLE 1

Preparation of a 9.3% Solution of Ethyllithium in Dibutyl Ether 14 g (2 mol) lithium powder (particle size 10 to 200 µm) was suspended in 300 g dibutyl ether in a double-jacketed reactor and cooled to 0° C. by means of cooling oil.

The ethyl chloride was charged from a steel cylinder. After a short time, the start of the reaction could be detected from the rise in temperature. The feed rate was so adjusted that the reaction proceeded as evenly as possible and the generated heat could be dissipated efficiently. Approximately 0.85 mol ethyl chloride was charged over a period of 240 minutes at a reaction temperature of approximately 0° C. There was then a wait of 90 minutes, until the heat of reaction had completely abated. The reaction could be easily monitored by withdrawing samples and determining the alkalinity.

The reaction batch was filtered and analysed. 280 g of a clear, colourless solution having a base content of 2.58 mmol/g was obtained. This corresponds to a 9.3% solution and to a yield (based on Li) of 72%.

The solution proved to be pyrophoric.

As a result of washing the Li/LiCl filter slurry, the yield was increased to 83%, which indicates a yield (based on ethyl chloride) of >97%.

EXAMPLE 2

Preparation of a 12% solution of ethyllithium in dibutyl ether

In a double-jacketed reactor, 23.9 g (3.44 mol) lithium powder (particle size 10 to 200 µm) was suspended in 300 g dibutyl ether and cooled to 0° C. by means of cooling oil.

The ethyl chloride was charged from a steel cylinder. After 15 minutes, the start of the reaction could be detected from the rise in temperature. The feed rate was so adjusted that the reaction proceeded as evenly as possible and the generated heat could be dissipated efficiently. Approximately 92 g (1.4 mol) ethyl chloride was charged over a period of 200 minutes at a reaction temperature of approximately 0° C. There was then a wait of 120 minutes, until the heat of reaction had completely abated. The reaction could be easily monitored by withdrawing samples and determining the alkalinity.

The reaction batch was filtered and analysed. 296.5 g of a clear, yellow solution having a base content of 3.45 mmol/g was obtained. This corresponds to a 12.4% solution and to a yield (based on Li) of 60%.

The solution had an oily consistency at room temperature and proved to be pyrophoric.

The yield (based on Li) was increased to 70% by washing the Li/LiCl filter slurry.

EXAMPLE 3

Dilution with Dibutyl Ether of a 12.4% Solution of Ethyllithium in Dibutyl Ether 200 g of the 12.4% solution of ethyllithium in dibutyl ether from Example 2 was diluted to 8% by adding 110 g dibutyl ether. This solution was not pyrophoric.

EXAMPLE 4

Dilution with Hexane of a 12.4% Solution of Ethyllithium in Dibutyl Ether 200 g of the 12.4% solution of ethyllithium in dibutyl ether from Example 2 was diluted to 8% by adding 110 g hexane. This solution was not pyrophoric.

EXAMPLE 5

Preparation of a 14.7% Solution of Ethyllithium in Dibutyl Ether 30 ml of the 12.4% solution of ethyllithium in dibutyl ether from Example 2 was concentrated to small volume at room temperature for a period of 2 days under a vacuum produced by an oil pump. A clear solution having a content of 14.7% EtLi remained.

What is claimed is:

1. A solution consisting essentially of ethyllithium and dibutyl ether, wherein the ethyllithium concentration is from 5 to 12 wt. %.

2. A solution consisting essentially of ethyllithium and dibutyl ether, wherein the ethyllithium concentration is from 7 to 8 wt. %.

3. A solution consisting essentially of ethyllithium, dibutyl ether, and a hydrocarbon, wherein the ratio of dibutyl ether to said hydrocarbon ranges from 99:1 to 25:75, wherein the solution is non-pyrophoric and contains 2 to 8 wt. % ethyllithium.

4. A solution according to claim 3, wherein said at least one hydrocarbon is selected from the group consisting of pentane, hexane, heptane, octane, cyclohexane, Tetralin, toluene, xylene, cumene and ethylbenzene.

5. The solution of claim 3, wherein the ethyllithium concentration ranges from 5 to 8 wt. %.

6. A solution according to claim 5, wherein said at least one hydrocarbon is selected from the group consisting of C5 to C12 acyclic aliphatic hydrocarbons, C5 to C12 cyclic aliphatic hydrocarbons, and C6 to C12 aromatic hydrocarbons.

7. A solution consisting of ethyllithium and dibutyl ether.

8. A solution consisting of ethyllithium and dibutyl ether, wherein the ethyllithium concentration is from 5 to 15 wt. %.

9. A solution consisting of ethyllithium and dibutyl ether, wherein the ethyllithium concentration is from 7 to 8 wt. %.

10. A solution consisting of ethyllithium, dibutyl ether, and a hydrocarbon, wherein the ratio of dibutyl ether to said hydrocarbon ranges from 99:1 to 25:75 , wherein the solution is non-pyrophoric and contains 2 to 8 wt. % ethyllithium.

11. A solution of claim 10, wherein the ethyllithium concentration ranges from 5 to 8 wt. %.

12. A solution according to claim 10, wherein said at least one hydrocarbon is selected from the group consisting of C5 to C12 acyclic aliphatic hydrocarbons, C5 to C12 cyclic aliphatic hydrocarbons, and C6 to C12 aromatic hydrocarbons.

13. A solution according to claim 10, wherein said at least one hydrocarbon is selected from the group consisting of pentane, hexane, heptane, octane, cyclohexane, Tetralin, toluene, xylene, cumene and ethylbenzene.

* * * * *